United States Patent [19]

Orlowski et al.

[11] 4,396,378
[45] Aug. 2, 1983

[54] METHOD FOR PREPARING CAVITIES IN TEETH FOR RESTORATION

[75] Inventors: Jan A. Orlowski, Altadena; Marvin N. Stark, Los Altos Hills; David V. Butler, West Covina, all of Calif.

[73] Assignee: Scientific Pharmaceuticals, Inc., Duarte, Calif.

[21] Appl. No.: 359,092

[22] Filed: Mar. 17, 1982

Related U.S. Application Data

[62] Division of Ser. No. 204,266, Nov. 5, 1980, abandoned.

[51] Int. Cl.³ .............................................. A61K 6/08
[52] U.S. Cl. ....................................... 433/217; 106/35;
260/998.11; 433/199; 433/201; 433/226;
433/228; 523/116; 523/117; 523/118
[58] Field of Search ................. 106/35; 433/228, 217,
433/226; 523/116, 117, 118

[56] References Cited

U.S. PATENT DOCUMENTS

| | | | |
|---|---|---|---|
| 2,630,397 | 3/1953 | Cowan et al. | 260/18 N |
| 2,788,287 | 4/1957 | Zweig | 260/18 N |
| 3,081,227 | 3/1963 | Wimberly | 106/35 |
| 3,087,904 | 4/1963 | Kalden | 433/217 |
| 3,266,147 | 8/1966 | Goldman | 433/217 |
| 3,469,317 | 9/1969 | Jarby | 433/217 |
| 3,868,447 | 2/1975 | Kliment | 433/228 |
| 4,240,832 | 12/1980 | Jandourek | 106/35 |

OTHER PUBLICATIONS

*Encyclopedia of Polymeric Science and Technology*, vol. 10, 1969, pp. 597–615.

*Primary Examiner*—Lorenzo B. Hayes
*Attorney, Agent, or Firm*—Cushman, Darby & Darby

[57] ABSTRACT

A solid fatty polyamide dissolved in a volatile organic solvent has been found effective for preparing cavities of teeth for restoration. For example, when this solution is applied to a cavity in the form of a dental cavity varnish, the organic solvent may be evaporated to leave behind a continuous polyamide film which is compatible with methacrylate resin type restoratives. Solid fatty polyamides are generally derived from the reaction product of partially polymerized unsaturated fatty acids with aliphatic diamines. The present invention relates to methods for preparing cavities with these polyamides as well as to compositions containing these polyamides.

15 Claims, No Drawings

METHOD FOR PREPARING CAVITIES IN TEETH FOR RESTORATION

This is a division, of application Ser. No. 204,266 filed Nov. 5, 1980, now abandoned.

BACKGROUND OF THE INVENTION

The present invention relates to compositions and methods for preparing teeth having cavities for restoration with a restorative material. A preferred composition may be characterized as a dental cavity varnish.

Cavity varnishes are commonly used in dentistry as adjuncts to restorative materials. Their role, in general, is to provide better pulp protection by sealing dental tubules thus preventing penetration of micro-organisms, reducing sensitivity to temperature changes and preventing penetration of potentially toxic substances from restorative materials that may damage or kill the pulp. The beneficial effects of cavity varnishes in preventing the occurrence of secondary caries, in elimination of post-operative tooth sensitivity and preservation of pulp vitality have been clinically well documented.

In their function, cavity varnishes are related to cavity liners (or bases) that are used for covering of the floor of the cavity in the deep restorations providing mechanical as well as anti-poison protection for the pulp and sometimes stimulating secondary dentine formation. While cavity liners are, by application requirements, of rather thick consistency and able to cure forming a relatively strong solid mass, cavity varnishes must be in the form of low to medium viscosity liquids that can be painted over the cavity wall. They should wet the dentine tissue well and leave, after drying, an adhesive film that seals the exposed dental tubules well.

Calcium hydroxide containing formulations are preferred as cavity liners for their compatability with all types of restorative materials, ability to stimulate secondary dentine formation and excellent compatability with the pulp. Unfortunately, commonly known calcium hydroxide type materials are generally unsuitable for use as cavity varnishes because of their consistency, inadequate mechanical properties when cured in a thin film, solubility in oral fluids and poor adhesion to dentine. Zinc oxide/eugenol type compositions, also commonly used as cavity liners, have the same disadvantages as calcium hydroxide formulations when it comes to consistency and mechanical properties and adhesion to dentine. In addition, they are incompatible with methacrylate resin based restorative materials, inhibiting their cure. This last characteristic is of special importance since so-called composite restoratives that use methacrylate monomers as binders are becoming the most frequently and universally used restorative materials.

Cavity varnishes, presently in use in dentistry, consist principally of solutions of solid materials in low boiling solvents. Most commonly used are solutions of natural gums such as copal or rosin in acetone or chloroform. They form solid films not through a chemical reaction but as a result of evaporation of the solvent. Adhesion to the dentine and sealing properties of these materials have been found adequate and, if proper caution is exercised, no toxic effect to the pulp may be expected from either the cured resin or the solvent.

The main limitation of natural gum-based cavity varnishes is their incompatability with methacrylate resin type restoratives. This limitation is considered very essential since methacrylate resins may leak toxic substances that may cause serious damage to the pulp. It is especially important, therefore, to seal dental tubules in order to prevent the penetration of toxic materials. The use of a liner under methacrylate resin based restoration is also desirable because these materials do not adhere to dentine and they shrink during cure, leaving the dentine unprotected. Marginal sealing is not always possible or sufficient to prevent secondary decays resulting from bacteria attack, tooth sensitivity or damage to the pulp caused by chemical substances present in the oral environment. Besides compatability with commonly used restorative materials and ability to adhere to dentine, the ideal varnish should meet the following requirements:

it should not be toxic or irritating.
it should cure or dry fast at body temperature or slightly higher.
it should be chemically resistant to the oral environment.
it should be easy to apply, preferably with a paint-on technique.

Until now, no dental varnish was available that would satisfy all these requirements.

SUMMARY OF THE INVENTION

The present invention relates to a solid fatty polyamide containing composition and a method for preparing a cavity of a tooth for restoration with such a composition. The polyamide containing composition is formed by dissolving a solid fatty polyamide in a volatile organic solvent. The method involves applying this composition to a cavity and evaporating the volatile solvent, thereby forming a film of the solid fatty polyamide in the cavity.

DETAILED DESCRIPTION OF THE INVENTION

This invention encompasses a new material for preparing cavities of teeth for restoration with a restorative material. This material is preferably in the form of a dental cavity varnish. It is compatible with all known types of restorative materials, non-toxic and non-irritating and chemically resistant to the oral environment. It also has a suitable physical form for easy application.

The cavity preparing material of the present invention comprises a solution of a solid fatty polyamide in a volatile organic solvent. The material may be applied to the cavity by any convenient means, preferably by a paint-on technique. The organic solvent must be sufficiently volatile to evaporate at body temperature to leave behind a solid film of the polyamide. Evaporation of the solvent may, thus, take place simply as a result of the application of the material to the cavity. Optionally, the rate of evaporation of this solvent may be increased by any suitable means, such as passing a gentle air stream over the treated cavity.

Solid fatty polyamides are non-nylon-type polyamides which may be derived from the reaction of partially polymerized unsaturated fatty acids or esters thereof with diamines. Polyamides of this type are discussed on pages 577 and 597–615 of the *Encyclopedia of Polymer Science and Technology*, Volume 10 (1969), the entire disclosure of which is incorporated herein by reference and relied upon. While not wishing to be limited to any reaction sequence for forming solid fatty polyamides, it will be appreciated that the chemical nature of solid fatty polyamides is more readily understood in view of representative chemical constituents of these compounds and the manner in which these compounds may be formed from these constituents. Accordingly, a discussion of an example of manner in which polyamides may be formed is given hereinbelow.

In a simplification of the overall process, unsaturated fatty acids may be used as the initial starting product for the formation of solid fatty polyamides. In a first reaction step, these unsaturated fatty acids may be partially polymerized to form mostly dimers and/or trimers. These dimers and/or trimers may then be reacted with diamines to form solid fatty polyamides. It will be understood that the above-mentioned unsaturated fatty acids may be replaced by the corresponding esters thereof (e.g., methyl esters) and the above-mentioned reaction sequence repeated to produce solid fatty polyamides. It will further be understood that these esters may be hydrolyzed to acids at any convenient stage of the reaction sequence. However, for the purposes of describing the chemical nature of solid fatty polyamides, the discussion which follows pertains primarily to acid reactants.

Unsaturated fatty acids are usually derived from vegetable sources but also may be derived from animal fats (e.g., fish oil). The most common unsaturated fatty acids are oleic, linoleic and linolenic which each contain a total of 18 carbon atoms. However, other unsaturated fatty acids are known such as palmitoleic ($C_{16}$), gadoleic ($C_{20}$) and eruic ($C_{22}$). Fatty acids all have a characteristic terminal carboxyl radical (—COOH). Thus, examples of unsaturated fatty acids may be represented by the formula $$R_1—COOH$$

where $R_1$ is an unsaturated aliphatic hydrocarbyl group having 15 to 21 carbon atoms.

Unsaturated fatty cids, having only one carboxylic acid functionality (—COOH), cannot be used, per se, to form polyamides. However, when these fatty acids are partially polymerized so as to form molecules having at least two carboxylic acid functionalities, these partially polymerized fatty acids may in turn be converted into polyamides by a polycondensation reaction with molecules which contain at least two amino groups. The partial polymerization of unsaturated fatty acids and their esters is discussed on pages 768–782 of the *Kirk-Othmer Encyclopedia of Chemical Technology*, third edition, volume 7 (1979), the entire disclosure of which is incorporated herein by reference and relied on. Thermal polymerization and clay-catalyzed polymerization are examples of two techniques for achieving the partial polymerization of unsaturated fatty acids. Generally, these techniques are designed to produce primarily dimers but lesser amounts of higher molecular weight molecules such as trimers are also produced. Unreacted monofunctional unsaturated fatty acids may also be present in the product stream.

Feedstocks for the partial polymerization reactions may be derived from natural products. For example, relatively unrefined tall oil fatty acids which contain a variety of unsaturated fatty acids may be subjected to a clay-catalyzed polymerization to obtain a variety of dimers and trimers. It is also possible to partially polymerize a more highly refined feedstock containing a higher percentage of a particular unsaturated fatty acid or even a single unsaturated fatty acid. Partially polymerized fatty acids or esters may be hydrogenated in order to obtain saturated compounds.

The product of the partial polymerization of unsaturated fatty acids may thus contain a variety of structures depending upon the degree of polymerization, the nature of the feedstock and possible subsequent hydrogenation. These structures may be acyclic, monocyclic or polycyclic. For example, the methyl ester of 9,11-linoleic acid may react with the methyl ester of 9,12-linoleic acid according to the following reaction sequence:

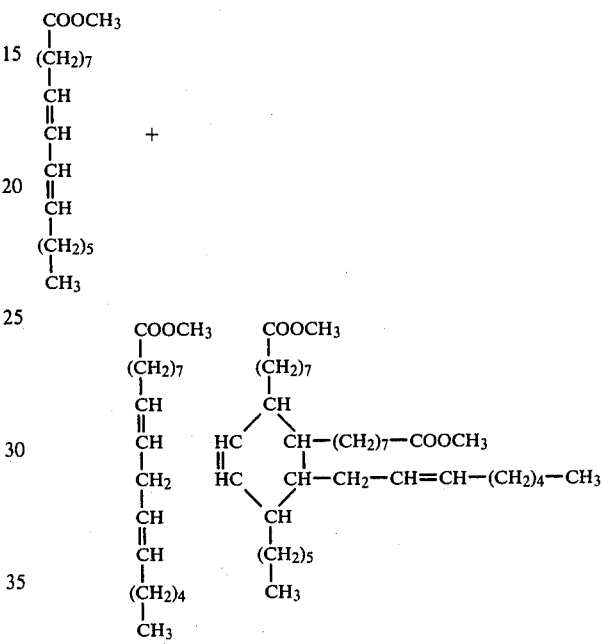

Accordingly, a partially polymerized fatty acid or ester may be a complex group of chemicals or it may be a single chemical entity.

Polyamides may be formed from partially polymerized fatty acids by a polycondensation reaction of these multifunctional acids with multifunctional amines. These multifunctional amines may be basically of two types: (i) diprimary amines which contain only two nitrogen atoms per molecule, each nitrogen atom being present in a primary amino group (—$NH_2$); and (ii) multifunctional amines which contain three or more nitrogen atoms, these nitrogen atoms being present in both primary amino groups and at least one secondary amino group (—NH—). The polycondensation product of partially polymerized unsaturated fatty acids with diprimary amines of the above-mentioned category (i) are basically relatively nonreactive solid polymers, while the polycondensation product of the acids with the secondary amino group-containing amines of the above-mentioned category (ii) are basically relatively reactive liquid polymers. Accordingly, solid fatty polyamides are formed from diamines containing only two primary amino groups. Preferably, these diamines are aliphatic diamines containing 2 to 8 carbon atoms such as ethylene diamine, propylene diamine, tetramethylene diamine, pentamethylene diamine, hexamethylene diamine, 3-methyl-hexamethylene diamine and octamethylene diamine. Preferred diamines are ethylene diamine and propylene diamine, especially ethylene diamine.

The product obtained by partially polymerizing unsaturated fatty acids may be purified or refined to various extents by removal of unwanted materials before solid fatty polyamides are prepared therefrom. Generally, this product is refined at least to the extent that only dimers and/or trimers remain. More particularly, the refined product may comprise from 0% to about 40% trimers and from about 60% to 100% dimers. Thus, solid fatty polyamides may be formed from acids which are one or more dimers or a mixture of dimers and trimers. Since unsaturated fatty acids containing 16 or more carbon atoms may be dimerized, partially polymerized fatty acids may contain at least 32 carbon atoms. Trimers of euric acid containing 66 carbon atoms are also possible. A preferred acid constituent of the solid fatty polyamides suitable for use in accordance with the present invention consists essentially of dimers of linoleic acid.

When the solid fatty polyamide is formed exclusively from a fatty acid dimer, the polyamide may be presented by the following formula:

where $R_1$ is an aliphatic hydrocarbyl moiety containing at least 30 carbon atoms and $R_2$ is an aliphatic hydrocarbyl moiety containing up to 8 carbon atoms. However, other formulae are possible. For instance, as previously mentioned, polyamides may be formed in part from trimers. Other monomers than the acidic or amino constituents previously mentioned are also possible as long as they do not destroy the desired properties of the resulting polyamide with respect to the intended use in accordance with the present invention. Thus, for example, minor amounts of the partially polymerized unsaturated fatty acid component of the polyamide may be replaced by diacids having from 4 to 8 carbon atoms between the 2 carboxylic acid functionalities. Such diacids include adipic, pimelic, azelaic, sebacic, terephthalic and hexahydroterephthalic.

The molecular weight of the solid fatty polyamide should be sufficiently low that the polyamide is soluble in the volatile organic solvent, yet sufficiently high that the polyamide forms an adequate film on the surface of the cavity after the solvent evaporates. Preferably, the molecular weight of the solid fatty polyamide should be from about 6000 to about 9000.

Suitable volatile organic solvents in which the solvent fatty polyamides may be dissolved include primary $C_1$–$C_4$ alcohols, e.g. methyl alcohol, ethyl alcohol, propyl alcohol, isopropyl alcohol and butyl alcohol, $C_5$–$C_8$ hydrocarbons, e.g. pentane, hexane, heptane and octane, methylene dichloride, chloroform, carbon tetrachloride and mixtures of these solvents. The solid fatty polyamides may preferably constitute from 5–40% by weight of the solution based upon the total weight of polyamide plus volatile organic solvent. The relative amounts of polyamide and solvent may also be expressed in terms of grams of polyamide per 100 ml of solvent. For example, the solid fatty polyamide solution may contain from about 5 grams to about 35 grams of polyamide per 100 ml of volatile organic solvent.

In addition to solid fatty polyamide dissolved in a volatile organic solvent, the composition of the present may also include various additives which are suitable for preparing the tooth for restoration. These additives include antibacterial and antiseptic additives, anti-fungal additives, anesthetic additives, additives which stimulate dentine formation and X-ray opaquing additives.

These additives may be present in amounts minimally sufficient to achieve their respective purposes but should not be present in quantities sufficiently large enough to destroy the desired preparation of the cavity for restoration. More particularly, the additives should not be present in quantities which would prevent the solid fatty polyamide from forming a restorative-compatible continuous film seal in the cavity.

Suitable antibacterial and antiseptic additives include benzalconium chloride, cetylpyridinium chloride and camphorated pentachlorophenol. Suitable anti-fungal agents include benzoic acid and salicyclic acid. Suitable anesthetic agents include benzocaine and benzyl alcohol. Suitable X-ray opaquing additives include barium sulphate, barium-containing glass and strontium-containing glass. Calcium hydroxide is a suitable additive for stimulating secondary dentine formation.

The additives to the polyamide/organic solvent solution are preferably non-volatile in that they do not evaporate along with the volatile organic solvent when the polyamide film is formed in the cavity. Since the restoration preparing compositions are preferably in the form of dental cavity varnishes which may be used to seal tubules along the sides of the cavity walls, the additives are preferably soluble in the volatile organic solvent to facilitate the paint-on application of the varnish. However, it will be appreciated that certain insoluble additives such as barium sulphate and calcium hydroxide may also be present. Thus, the cavity preparations may range in viscosity from relatively thin flowable liquids to rather thick pastes. The paste-type materials, however, are generally suitable for sealing only the base portions of the cavity. It is noted that dental cavity varnishes intended for use in sealing tubules along the side walls of cavities should preferably be free of calcium hydroxide, because when present in sufficient quantities calcium hydroxide may be dissolved by water in the mouth environment leaving voids which permeate the polyamide film seal.

The cavity preparation may be applied as a single coating or in multiple coatings. When multiple coatings are applied, sufficient time between coatings may be provided to permit the volatile organic solvent to fully or partially evaporate. The coating thickness should be sufficiently large to present an effective seal but sufficiently small to permit sufficient space in the cavity for application of the restorative material.

The following examples are given for the purpose of further explanation of the nature of this invention only. They should not be understood as limiting the scope of the invention as defined in the claims.

EXAMPLE I

A polyamide resin being a reaction product of dimerized linoleic acid with ethylenediamine and having molecular weight of about 8,000, softening point of 110° C. and Brookfield viscosity of 16 Poises at 160° C. was dissolved in a solvent containing of a mixture of 66% by weight of isopropyl alcohol and 33% of n-hexane. The solution containing 20 g of resin in 100 cc of solvent represented a pale yellow clear liquid having suitable flowing properties and consistency for application as a cavity varnish. Microscopic observation of the dentin tissue coated with this varnish shows well sealed dental tubules and no separation after soaking in 37° C. water.

EXAMPLE II 15 g of polyamide resin as described in Example I was dissolved in an azeotropic mixture of 62 g of ethyl alcohol and 32 g toluene. The properties of the varnish from the point of view of ease of application and performance were most satisfactory.

EXAMPLE III 20 g of a polyamide resin being a reaction product of dimerized linoleic acid with ethylenediamine and having molecular weight of about 8,000, softening point of 110° C. and Brookfield viscosity of 16 Poises at 160° C. was dissolved in 100 g of solvent consisting of a mixture of 66% by weight of isopropyl alcohol and 33% of n-hexane. To thus obtained solution, 2.5 g of fumed silica and 5 g of precipitated $Co(OH)_2$ was added while stirring vigorously. The resulting varnish is in the form of suspension. It has the ability of sealing dental tubules with no signs of separation after soaking in 37° C. water.

All percentages expressed herein are by weight unless otherwise specified.

While certain representative embodiments and details have been shown for the purposes of illustrating the invention, it will be apparent to those skilled in the art that various changes and modifications may be made therein without departing from the spirit or scope of the invention. It will further be understood that the invention may comprise, consist essentially of or consist of the steps or materials recited herein.

What is claimed is:

1. A method for preparing a tooth having a cavity for restoration with a restorative material, said method comprising the steps of:
   (i) applying to the cavity at least one solution comprising at least one solid fatty polyamide dissolved in a volatile organic solvent; and
   (ii) forming a solid, hardened film of said polyamide in said cavity by evaporation of said solvent, said polyamide consisting essentially of the reaction product of at least one partially polymerized unsaturated fatty acid with at least one aliphatic diamine, said partially polymerized fatty acid having at least 32 carbon atoms and at least two carboxylic acid groups, said aliphatic diamine having 2–8 carbon atoms and two primary amino groups, and said polyamide having a molecular weight from about 6000 to about 9000.

2. A method according to claim 1, wherein said partially polymerized unsaturated fatty acids consist of from about 40% to about 100% of dimers of at least one of said unsaturated fatty acids and from 0% to about 40% of trimers of at least one of said unsaturated fatty acids.

3. A method according to claim 1, wherein said organic solvent is selected from the group consisting of primary $C_1$–$C_4$ alcohols, $C_5$–$C_8$ hydrocarbons, methylenedichloride, chloroform, carbon tetrachloride and mixtures of said solvents.

4. A method according to claim 1, wherein said polyamide is the reaction product of dimerized linoleic acid with ethylene diamine.

5. A method according to claim 1, wherein said solution comprises from about 5 to about 35 grams of said polyamide per 100 ml of said solvent.

6. A method according to claim 1, wherein said step (i) comprises painting a solution which is a dental cavity varnish on the sides of said cavity, whereby when said polyamide film is formed in accordance with said step (ii) the exposed dental tubules of the tooth are sealed.

7. A method according to claim 1 wherein the composition employed consists essentially of:
   (i) at least one solid fatty polyamide;
   (ii) a volatile organic solvent, said polyamide (i) being dissolved in said solvent; and
   (iii) at least one non-volatile material suitable for preparing said tooth for restoration selected from the group consisting of antibacterial and antiseptic additives, antifungal additives, anesthetic additives, additives which stimulate secondary dentine formation and X-ray opaquing additives.

8. A method according to claim 7, wherein said non-volatile material (iii) is selected from the group consisting of:
   (a) antibacterial and antiseptic additives selected from the group consisting of benzalconium chloride, cetylpyridinium chloride, and camphorated pentachlorophenol;
   (b) anti-fungal agents selected from the group consisting of benzoic acid and salicylic acid;
   (c) anesthetic agents selected from the group consisting of benzocaine and benzyl alcohol;
   (d) an additive for stimulating secondary dentine formation which is calcium hydroxide; and
   (e) X-ray opaquing additives selected from the group consisting of barium sulphate, barium containing glass and strontium containing glass.

9. A method according to claim 7 wherein the solution is a dental cavity varnish and step (i) comprising painting said varnish on the sides of the cavity, whereby when said polyamide is formed in accordance with step (ii) the exposed dental tubules of the tooth are sealed and wherein said non-volatile material (iii) is fully dissolved in said volatile liquid (ii), and wherein said varnish is free of calcium hydroxide.

10. A process according to claim 7 wherein the composition includes calcium hydroxide as component (iii) for stimulating secondary dentine formation.

11. A process according to claim 1 wherein the composition includes calcium hydroxide as an additive for stimulating secondary dentine formation.

12. A process according to claim 1 wherein the composition contains an antibacterial and antiseptic additive selected from the group consisting of benzalconium chloride, cetylpyridinium chloride and camphorated pentachlorophenol.

13. A process according to claim 1 wherein the composition contains an anesthetic agent selected from the group consisting of benzocaine and benzyl alcohol.

14. A process according to claim 1 wherein the composition contains an x-ray opaquing additive selected from the group consisting of barium sulphate, barium containing glass and strontium containing glass.

15. A method according to claim 1 wherein the polyamide consists of the stated reaction product.

* * * * *